(12) United States Patent
Quan et al.

(10) Patent No.: US 11,939,610 B2
(45) Date of Patent: Mar. 26, 2024

(54) PROTEASE COMPOSITIONS AND METHODS OF USE THEREOF

(71) Applicant: NeoGeneStar LLC, Warren, NJ (US)

(72) Inventors: Nancy Quan, Warren, NJ (US); Zheng Wang, Bridgewater, NJ (US); Thor W. Nilsen, Stirling, NJ (US)

(73) Assignee: NeoGeneStar LLC, Warren, NJ (US)

( * ) Notice: Subject to any disclaimer, the term of this patent is extended or adjusted under 35 U.S.C. 154(b) by 45 days.

(21) Appl. No.: 17/476,767

(22) Filed: Sep. 16, 2021

(65) Prior Publication Data

US 2022/0081683 A1 Mar. 17, 2022

Related U.S. Application Data

(60) Provisional application No. 63/079,188, filed on Sep. 16, 2020.

(51) Int. Cl.
*C12N 9/58* (2006.01)

(52) U.S. Cl.
CPC ........ *C12N 9/58* (2013.01); *C12Y 304/21064* (2013.01)

(58) Field of Classification Search
CPC ...................................................... C12N 9/58
See application file for complete search history.

(56) References Cited

U.S. PATENT DOCUMENTS

2016/0312157 A1* 10/2016 Haugaard .......... C11D 3/38627

FOREIGN PATENT DOCUMENTS

WO WO-2016061025 A1 * 4/2016 ................ C08J 5/18

* cited by examiner

*Primary Examiner* — Yong D Pak
(74) *Attorney, Agent, or Firm* — FOX ROTHSCHILD LLP

(57) ABSTRACT

This disclosure describes a novel, ready-to-use protease composition in the form of a film or pouch composition. The protease composition can be used for stabilizing a biological sample containing a nucleic acid molecule for storage or transportation. It allows quick removal of protein contamination in the biological sample, thus facilitating sample preparation for nucleic acid detection or extraction.

19 Claims, 1 Drawing Sheet

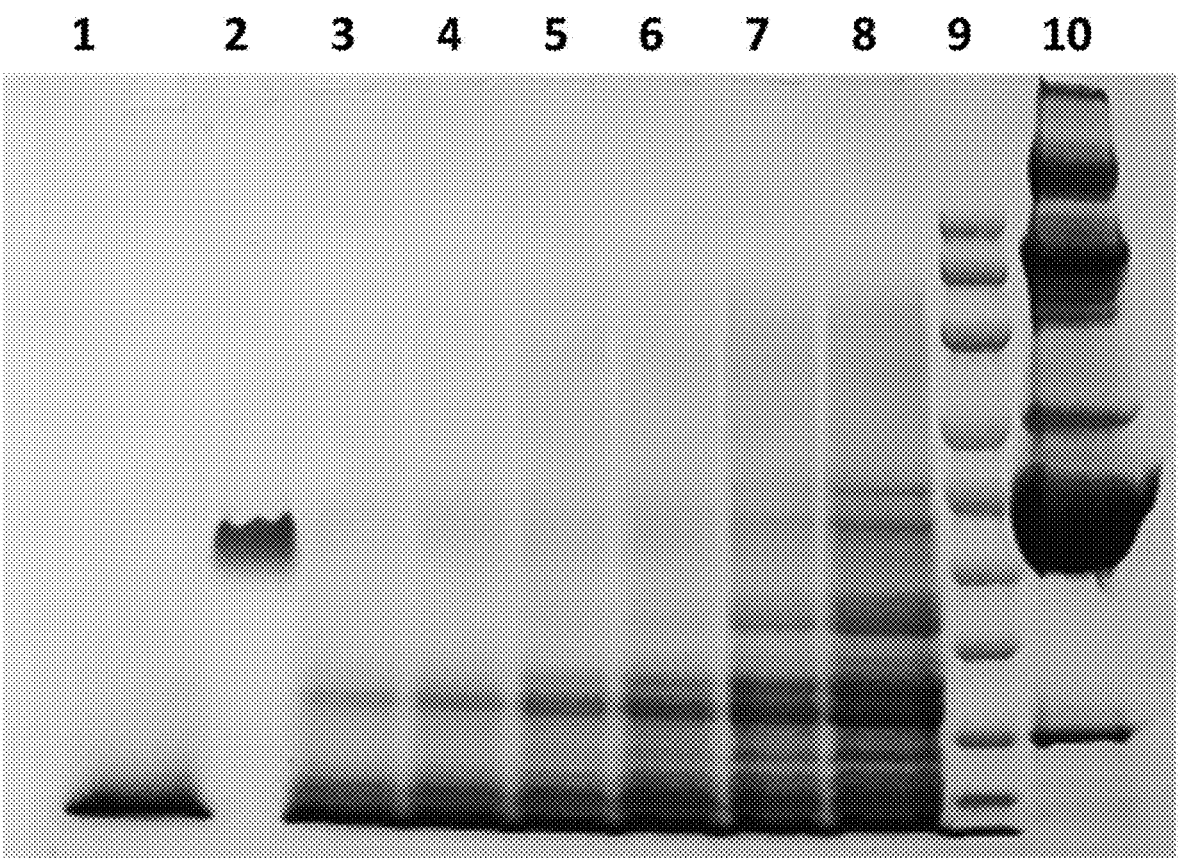

PROTEASE COMPOSITIONS AND METHODS OF USE THEREOF

CROSS-REFERENCE TO RELATED APPLICATIONS

This application claims priority under 35 U.S.C. § 119(e) to U.S. Provisional Patent Application No. 63/079,188, filed Sep. 16, 2020. The foregoing application is incorporated by reference herein in its entirety.

FIELD OF THE INVENTION

This disclosure relates generally to a novel, ready-to-use protease compositions and more specifically to protease compositions in film and pouch forms and methods of use thereof.

BACKGROUND OF THE INVENTION

The detection and separation of nucleic acid is an important step in many biochemical and diagnostic procedures. For example, separation of nucleic acids from complex mixtures in which they are often present is frequently necessary for detection, cloning, sequencing, amplification, hybridization, cDNA synthesis, etc. However, the presence of large amounts of cellular debris and other material such as proteins, lipid or carbohydrates in such complex mixtures often interfere with many downstream reactions and techniques used in molecular biology. In particular, the methods for detection and isolation of nucleic acids from complex mixtures are important for the processes that rely on identification of nucleic acids, such as diagnosis of microbial and viral infections, forensic science, tissue and blood typing, detection of genetic variations and cancer, etc.

Nucleic acid from a biological fluid is extremely sensitive to rapid degradation from DNase or RNases that are present in most biological fluids, such as blood, urine or saliva. Thus, the presence of DNase or RNases could significantly undermine the integrity of nucleic acids that is critically important for downstream analysis. The existing methods for the isolation of nucleic acids from a complex starting material, such as blood, blood products, cells or tissues, and other biological fluids, are laborious and cumbersome. The procedures for nucleic acid isolation/purification generally involve multiple steps, including lysis of the biological material by pretreating samples with protein degrading enzymes in the presence of detergent, followed by a lysis/bind step with a chaotropic agent and allowing the nucleic acid to bind to a solid support, whereupon the nucleic acid may be detected and/or extracted from the starting material.

In addition, the existing nucleic acid purification method includes a pretreatment step for complex starting material, which generally requires protease treatment or use of nucleic acid stabilization reagents. For example, many commercially available reagents/kits, such as DNA/RNA Shield, RNAlater, or RNAprotect, etc, involve protease or chemical reagents to deactivate nuclease(s) in biological fluids. However, the protein degrading enzymes, such as proteinase K, are usually biologically unstable in the liquid form, and there is a need for improving the stability of protein degrading enzymes. Similarly, some detergents in liquid form can be easily oxidized, resulting in loss of function. On the other hand, detergents in dry powder form are difficult to be disposed in a required dose amount in a sample collection device.

Accordingly, there is a need for methods and reagents which provide ready-to-use reagents for a single sample that allow for more efficient stabilization, detection and/or isolation of nucleic acids for storage, conservation, transportation, and subsequent detection.

SUMMARY OF THE INVENTION

This disclosure addresses the need mentioned above in a number of aspects. In one aspect, this disclosure provides a kit comprising: a protease composition comprising a protease, a polymer matrix formed of a polymer, and optionally an instruction material. The polymer matrix is in the form of: (i) a film where the protease is distributed therewithin; or (ii) a pouch where the protease is encapsulated therein, wherein the polymer matrix is dissolvable in an aqueous phase and capable of releasing the protease from the kit upon contacting the aqueous phase.

In some embodiments, the protease is a serine protease. In some embodiments, the protease is selected from proteinase K, trypsin, chymotrypsin, papain, pepsin, pronase, endoproteinase Lys-C and cyanogen bromide, neutral, heat-sensitive serine protease (NHSSP), and mixtures thereof. In some embodiments, the protease is proteinase K.

In some embodiments, the polymer is selected from poly(vinyl) alcohol (PVOH), sodium carboxymethyl cellulose (NaCMC), hydroxyethyl cellulose (HEC), hydroxypropyl cellulose (HPC), hydroxypropylmethylcellulose (HPMC), polyvinylpyrrolidone (PVP), hydroethylmethyl cellulose (HEMP), pullulan, gelatin, modified starch, polyethylene oxide, polyacrylate, and combinations thereof.

In some embodiments, the protease composition further comprises a detergent. In some embodiments, the detergent is selected from deoxycholate, sodium dodecyl sulfate (SDS), Lithium dodecyl sulfate (LDS), N-lauroylsarcosine, Sarkosyl, cetyltrimethylammoniumbromide (CTAB), Triton (e.g., Triton X-15, X-35, X-45, X-100, X-102, X-104, X-114, X-165, X-305, X-405, X-705), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Polysorbate 80 (Tween® 80), polyethylene glycol sorbitan monooleate, polidocanol, n-dodecyl beta-D-maltoside (DDM), NP-40, nonylphenyl polyethylene glycol, $C_{12}E_8$ (octaethylene glycol n-dodecyl monoether), hexaethyleneglycol mono-n-tetradecyl ether $(C_{14}EO_6)$, octyl-beta-thioglucopyranoside (octyl thioglucoside, OTG), Genapol® X-080, Genapol® X-100, Emulgen, and polyoxyethylene 10 lauryl ether $(C_{12}E_{10})$, CHAPS, zwitterion 3-14, 3-[(3-cholamidopropyl)dimethylammonio]-1-propancsulfonate, and combinations thereof.

In some embodiments, the protease composition further comprises a buffer. In some embodiments, the buffer is selected from sodium citrate, sodium acetate, acetic acid, sodium carbonate, sodium bicarbonate, MES, Tris, Bis-Tris, ADA, aces, PIPES, MOPSO, Bis-Tris Propane, PBS, BES, MOPS, TES, HEPES, DIPSO, MOBS, TAPSO, TRIZMA, HEPPSO, POPSO, TEA, EPPS, Tricine, Gly-Gly, Bicine, HEPBS, TAPS, AMPD, TABS, AMPSO, CHES, CAPSO, AMP, CAPS, CABS, and combinations thereof.

In some embodiments, the protease composition has a pH of between about 4.0 and about 13.0.

In some embodiments, the protease composition further comprises an additional agent. In some embodiments, the additional agent comprises cetyltrimethylammonium bromide (CTAB), EDTA, EGTA, DTT, 2-mercaptoethanol, ammonium sulfate, polyethylene glycol, a coloring agent, glycerin, guanidinium chloride, guanidinium thiocyanate, urea, calcium salt, sodium salt, potassium salt, magnesium salt, tetradecyl-trimethyl-ammonium bromide (TTAB), Tetradecyl-trimethyl-ammonium oxalate (TTAO), tartaric acid, sodium hypochlorite, sodium dichloroisocyanurate, potassium citrate, 1-ethyl-2-pyrrolidone, peracetic acid, sodium bicarbonate or a mixture thereof.

In some embodiments, polymer matrix is in an amount of between about 10 wt % and about 34 wt % (e.g., 10 wt %, 12 wt %, 14 wt %, 16 wt %, 18 wt %, 20 wt %, 22 wt %, 24 wt %, 26 wt %, 28 wt %, 30 wt %, 32 wt %, 34 wt %). In some embodiments, the polymer matrix is in an amount of between about 15 wt % and about 30 wt % (e.g., 16 wt %, 18 wt %, 20 wt %, 22 wt %, 24 wt %, 26 wt %, 28 wt %, 30 wt %). In some embodiments, the protease is in an amount of between about 0.5 wt % and about 85 wt % (e.g., 2 wt %, 4 wt %, 6 wt %, 8 wt %, 10 wt %, 12 wt %, 14 wt %, 16 wt %, 18 wt %, 20 wt %, 22 wt %, 24 wt %, 26 wt %, 28 wt %, 30 wt %, 32 wt %, 34 wt %, 36 wt %, 38 wt %, 40 wt %, 42 wt %, 44 wt %, 46 wt %, 48 wt %, 50 wt %, 52 wt %, 54 wt %, 56 wt %, 58 wt %, 60 wt %, 62 wt %, 64 wt %, 66 wt %, 68 wt %, 70 wt %, 72 wt %, 74 wt %, 76 wt %, 78 wt %, 80 wt %, 82 wt %, 84 wt %, 85 wt %). In some embodiments, the detergent is in an amount of between about 0.2 wt % and about 30 wt % (e.g., 1 wt %, 3 wt %, 5 wt %, 7 wt %, 9 wt %, 11 wt %, 13 wt %, 15 wt %, 17 wt %, 19 wt %, 21 wt %, 23 wt %, 25 wt %, 27 wt %, 29 wt %, 30 wt %).

In some embodiments, the protease composition comprises: (i) between about 1 wt % and about 80 wt % of proteinase K; (ii) between about 5 wt % and about 34 wt % of PVOH; (iii) between about 0.2 wt % and about 80 wt % of SDS; and (iv) between about 0 wt % and about 10 wt % of glycerine.

In some embodiments, the protease composition has a thickness of between about 1 µm and about 500 mm.

In another aspect, this disclosure also provides a kit comprising a protease composition as described above. In some embodiments, the kit further comprises a detergent provided in a separate container or a separate compartment from the protease composition.

In another aspect, this disclosure further provides a method of degrading a protein in a sample. The method comprises contacting the sample with the kit as described above. In some embodiments, the sample is a biological sample comprising a nucleic acid molecule. In some embodiments, the biological sample comprises human or animal tissue, plasma, serum, blood, saliva, amniotic fluid, aqueous humor, vitreous humor, bile, breast milk, cerebrospinal fluid, cerumen, chyle, chyme, endolymph, perilymph, diarrhea, stool, female ejaculate, gastric acid, gastric juice, lymph, mucus, pericardial fluid, peritoneal fluid, pleural fluid, purulent exudate, rheum, cebum, semen, sputum, synovial fluid, lacrimal fluid, sweat, vaginal secretions, vomit, urine, cultured cell or supernatant, or plant or plant part thereof.

In yet another aspect, this disclosure additionally provides a method of stabilizing nucleic acid molecules from a sample containing a protein. The method comprises: (a) contacting the sample with a kit described above; and (b) incubating the mixture for a predetermined period of time, thereby stabilizing the nucleic acid for transportation, conservation or storage; and (c) optionally detecting and/or isolating the nucleic acid molecule from the sample.

The foregoing summary is not intended to define every aspect of the disclosure, and additional aspects are described in other sections, such as the following detailed description.

The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

The single FIGURE shows the activity of proteinase K as provided in the disclosed film composition on human plasma. Proteinase K in different amounts (0.2 mg, 0.3 mg, 0.5 mg, 0.6 mg, 1 mg, and 1.2 mg) was mixed with the plasma sample and incubated at 55° C. for 30 minutes.

DETAILED DESCRIPTION OF THE INVENTION

This disclosure describes a novel, ready-to-use protease composition in the form of a film or pouch composition. The protease composition can be used for degrading protein including nuclease, therefore stabilizing a biological sample containing a nucleic acid molecule for storage or transportation. It also allows quick removal of protein contamination in the biological sample, thus facilitating sample preparation for nucleic acid detection or extraction.

A. FILM OR POUCH COMPOSITIONS

In one aspect, this disclosure provides a kit comprising: a protease composition comprising a protease, a polymer matrix formed of a polymer, and optionally an instruction material. The polymer matrix is in the form of: (i) a film where the protease is distributed therewithin; or (ii) a pouch where the protease is encapsulated therein, wherein the polymer matrix is dissolvable in an aqueous phase and capable of releasing the protease from the kit upon contacting the aqueous phase.

In some embodiments, polymer matrix is in an amount of between about 5 wt % and about 34 wt % (e.g., 5 wt %, 10 wt %, 12 wt %, 14 wt %, 16 wt %, 18 wt %, 20 wt %, 22 wt %, 24 wt %, 26 wt %, 28 wt %, 30 wt %, 32 wt %, 34 wt %). In some embodiments, the polymer matrix is in an amount of between about 15 wt % and about 30 wt % (e.g., 16 wt %, 18 wt %, 20 wt %, 22 wt %, 24 wt %, 26 wt %, 28 wt %, 30 wt %).

It will be understood that the term "film" includes thin films and sheets, in any shape, including rectangular, square, or other desired shape. The films described herein may be any desired thickness and size. For example, the films may have a relatively thin thickness of between about 1 µm and about 500 mm (e.g., between about 5 µm and about 400 mm, between about 2 µm and about 300 mm, between about 1 µm and about 200 mm, between about 1 µm and about 100 mm, between about 1 µm and about 50 mm, between about 1 µm and about 25 mm, between about 1 µm and about 10 mm, between about 1 µm and about 1 mm, between about 1 µm and about 500 µm). Films may be in a single layer or they may be multi-layered, including laminated films.

In some embodiments, the polymer matrix is water-soluble. As used herein, the term "water-soluble" refers to substances that are at least partially dissolvable in a solvent, including but not limited to water. The term "water-soluble" does not necessarily mean that the substance is 100% dissolvable in the solvent. The term "water-insoluble" refers to substances that are not dissolvable in a solvent, including but not limited to water. Solvents may include water, or alternatively may include other polar solvents by themselves or in combination with water.

In some embodiments, the film compositions comprising a polymer matrix may be produced by a combination of at least one protease, at least one polymer and a solvent, optionally including other fillers known in the art. The solvent may be water, a polar organic solvent including, but not limited to, ethanol, isopropanol, acetone, or any combination thereof. In some embodiments, the solvent may be a non-polar organic solvent, such as methylene chloride. The film may be prepared by utilizing a selected casting or deposition method and a controlled drying process. For example, the film may be prepared through controlled drying processes, which include application of heat and/or radiation energy to the wet film matrix to form a viscoelastic structure, thereby controlling the uniformity of content of the film. Such processes are described in more detail in commonly assigned U.S. application Ser. No. 10/074,272, filed on Feb. 14, 2002, and published as U.S. Patent Publication No. 2003/0107149 A1, the contents of which are incorporated herein by reference in their entireties. Alternatively, the film compositions may be extruded as described in commonly assigned U.S. application Ser. No. 10/856,176, filed on May 28, 2004, and published as U.S. Patent Publication No. 2005/0037055 A1, the contents of which are incorporated herein by reference in their entireties.

In some embodiments, the polymer matrix is useful for creating a packet to contain a protease composition therein, thereby forming a pouch. The polymer matrix can also be used to make a pouch composition with two or more compartments made of the same polymer matrix or in combination with polymer matrices of other polymeric materials. The compartments of multi-compartment pouches may be of the same or different size(s) and/or volume(s). The compartments of the present multi-compartment pouches can be separate or conjoined in any suitable manner.

a. Proteases

The term "protease," "peptidase," or "proteinase," as used herein, refers to an enzyme that catalyzes (increases the rate of) proteolysis, the breakdown of proteins into smaller polypeptides or single amino acids. They do this by cleaving the peptide bonds within proteins by hydrolysis, a reaction where water breaks bonds.

The protease, as described above, can be any one of serine proteases, cysteine proteases, threonine proteases, aspartic proteases, glutamic proteases, metalloproteases, and asparagine peptide lyases. In some embodiments, the protease composition may comprise subtilisin, acid protease, alkaline protease, proteinase, peptidase, endopeptidase, exopeptidase, thermolysin, papain, pepsin, trypsin, pronase, carboxylase, serine protease, glutamic acid protease, aspartic protease, cysteine protease, threonine protease, a metalloprotease, or combinations thereof.

In some embodiments, the protease is a serine protease. In some embodiments, the protease is selected from proteinase K, trypsin, chymotrypsin, papain, pepsin, pronase, endoproteinase Lys-C and cyanogen bromide, neutral, heat-sensitive serine protease (NHSSP), and mixtures thereof. In some embodiments, the protease is proteinase K. By way of example, addition of proteinase K to nucleic acid preparations rapidly inactivates DNase and RNase that might otherwise degrade the DNA or RNA during nucleic acid detection and purification procedure. Proteinase K is active in the presence of chemicals, such as sodium dodecyl sulfate (SDS). Proteinase K can be used in the isolation of highly native, undamaged DNA or RNA, since most microbial or mammalian DNase and RNase are rapidly hydrolyzed by the enzyme, for example, in the presence of 0.5-1% SDS.

In some embodiments, the protease is in an amount of between about 0.5 wt % and about 85 wt % (e.g., 2 wt %, 4 wt %, 6 wt %, 8 wt %, 10 wt %, 12 wt %, 14 wt %, 16 wt %, 18 wt %, 20 wt %, 22 wt %, 24 wt %, 26 wt %, 28 wt %, 30 wt %, 32 wt %, 34 wt %, 36 wt %, 38 wt %, 40 wt %, 42 wt %, 44 wt %, 46 wt %, 48 wt %, 50 wt %, 52 wt %, 54 wt %, 56 wt %, 58 wt %, 60 wt %, 62 wt %, 64 wt %, 66 wt %, 68 wt %, 70 wt %, 72 wt %, 74 wt %, 76 wt %, 78 wt %, 80 wt %, 82 wt %, 84 wt %, 85 wt %).

b. Polymers

The polymer included in the protease compositions may be water-soluble or water-swellable or a combination of one or more either water-soluble, water-swellable or water-insoluble polymers. The polymer may include cellulose or a cellulose derivative. Specific examples of useful water-soluble polymers include, but are not limited to, polyethylene oxide, pullulan, hydroxypropylmethylcellulose, hydroxyethylcellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, Arabic gum, polyacrylic acid, methylmethacrylate co-polymer, carboxyvinyl co-polymers, starch, gelatin, and combinations thereof. Examples of useful water-insoluble polymers include, but are not limited to, ethylcellulose, hydroxypropyl ethylcellulose, cellulose acetate phthalate, hydroxypropyl methylcellulose phthalate, and combinations thereof.

As used herein, the phrase "water-soluble polymer" and variants thereof refer to a polymer that is at least partially soluble in water, and desirably fully or predominantly soluble in water, or absorbs water. Polymers that absorb water are often referred to as being water-swellable polymers. The materials useful with the present invention may be water-soluble or water-swellable at room temperature and other temperatures, such as temperatures exceeding room temperature. Moreover, the materials may be water-soluble or water-swellable at pressures less than atmospheric pressure. In some embodiments, films formed from such water-soluble polymers may be sufficiently water-soluble to be dissolvable upon contact with bodily fluids.

Other polymers useful for incorporation into the protease compositions include biodegradable polymers, co-polymers, block polymers, and combinations thereof. It is understood that the term "biodegradable" is intended to include materials that chemically degrade, as opposed to materials that physically break apart (i.e., biodegradable materials). Among the known useful polymers or polymer classes which meet the above criteria are: poly(glycolic acid) (PGA), poly(lactic acid) (PLA), polydioxanes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and co-polymers thereof. Additional useful polymers include, without limitation, stereopolymers of L- and D-lactic acid, co-polymers of bis(p-carboxyphenoxy)propane acid and sebacic acid, sebacic acid co-polymers, co-polymers of caprolactone, poly(lactic acid)/poly(glycolic acid)/polyethyleneglycol co-polymers, co-polymers of polyurethane and (poly(lactic acid), co-polymers of polyurethane and poly(lactic acid), co-polymers of α-amino acids, co-polymers of α-amino acids and caproic acid, co-polymers of α-benzyl glutamate and polyethylene glycol, co-polymers of succinate and poly (glycols), polyphosphazene, polyhydroxy-alkanoates, and mixtures thereof.

Other polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a co-polymer of 50% lactide and 50% glycolide with a melting point within the range of 338°-347° F. (170°-175° C.).

In some embodiments, the polymers, co-polymers or derivatives thereof suitable for use in the protease compositions are selected from polyvinyl alcohols, polyvinyl pyrrolidone, polyalkylene oxides, polyacrylic acid, cellulose, cellulose ethers, cellulose esters, cellulose amides, polyvinyl acetates, polycarboxylic acids, and salts, polyaminoacids or peptides, polyamides, polyacrylamide, co-polymers of maleic/acrylic acids, polysaccharides including starch and gelatin, natural gums such as xanthan, and carrageenans. For example, polymers can be selected from polyacrylates and water-soluble acrylate co-polymers, methylcellulose, carboxymethylcellulose to sodium, dextrin, ethylcellulose, hydroxyethylcellulose, hydroxypropyl methylcellulose, maltodextrin, polymethacrylates, and combinations thereof, or selected from polyvinyl alcohols, polyvinyl alcohol co-polymers, and hydroxypropyl methylcellulose (HPMC), and combinations thereof.

In some embodiments, the polymer is selected from poly(vinyl) alcohol (PVOH), sodium carboxymethyl cellulose (NaCMC), hydroxyethyl cellulose (HEC), hydroxypropyl cellulose (HPC), hydroxypropylmethylcellulose (HPMC), polyvinylpyrrolidone (PVP), hydroethylmethyl cellulose (HEMP), pullulan, gelatin, modified starch, polyethylene oxide, polyacrylate, and combinations thereof.

c. Detergents

In some embodiments, the protease composition further comprises a detergent. The detergent can be a surfactant or a mixture of surfactants. The detergent may include cationic, anionic, zwitterionic, and amphoteric surfactants such as are known in the art. See, e.g., McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973. A wide variety of anionic surfactants are also useful herein. See, e.g., U.S. Pat. No. 3,929,678, to Laughlin et al., issued Dec. 30, 1975.

Examples of nonionic detergents include triton, such as the Triton® X series (Triton® X-100 t-Oct-$C_6H_4$—(OCH$_2$—CH$_2$)xOH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, $C_{12}E_8$ (octaethylene glycol n-dodecyl monoether), hexaethyleneglycol mono-n-tetradecyl ether ($C_{14}EO_6$), octyl-beta-thioglucopyranoside (octyl thioglucoside, OTG), Emulgen, and polyoxyethylene 10 lauryl ether ($C_{12}E_{10}$). Examples of ionic detergents (anionic or cationic) include deoxycholate, sodium dodecyl sulfate (SDS), N-lauroylsarcosine, and cetyltrimethylammonium bromide (CTAB). A zwitterionic reagent may also be used in the purification schemes of the present disclosure, such as Chaps, zwitterion 3-14, and 3 [(3-cholamidopropyl)dimethylammonio]-1-propanesulfonate.

In some embodiments, the detergent is selected from deoxycholate, sodium dodecyl sulfate (SDS), Lithium dodecyl sulfate (LDS), N-lauroylsarcosine, Sarkosyl, cetyltrimethylammoniumbromide (CTAB), Triton® X series (Triton® X-100 t-Oct-$C_6H_4$—(OCH$_2$—CH$_2$)xOH, x=9-10, Triton® X-100®, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Polysorbate 80 (Tween® 80), polyethylene glycol sorbitan monooleate, polidocanol, n-dodecyl beta-D-maltoside (DDM), NP-40, nonylphenyl polyethylene glycol, $C_{12}E_8$ (octaethylene glycol n-dodecyl monoether), hexaethyleneglycol mono-n-tetradecyl ether ($C_{14}EO_6$), octyl-beta-thioglucopyranoside (octyl thioglucoside, OTG), Genapol® X-080, Genapol® X-100, Emulgen, and polyoxyethylene 10 lauryl ether ($C_{12}E_{10}$), CHAPS, zwitterion 3-14, 3-[(3-cholamidopropyl)dimethylarnmonio]-1-propancsulfonate, and combinations thereof.

In some embodiments, the detergent is in an amount of between about 0.2 wt % and about 30 wt % (e.g., 1 wt %, 3 wt %, 5 wt %, 7 wt %, 9 wt %, 11 wt %, 13 wt %, 15 wt %, 17 wt %, 19 wt %, 21 wt %, 23 wt %, 25 wt %, 27 wt %, 29 wt %, 30 wt %).

In some embodiments, the protease composition comprises: (i) between about 1 wt % and about 80 wt % of proteinase K; (ii) between about 5 wt % and about 34 wt % of PVOH; (iii) between about 0.2 wt % and about 80 wt % of SDS; and (iv) between about 0 wt % and about 10 wt % of glycerine.

d. Buffers

The protease compositions may further contain a buffer so as to control the pH of the protease composition or, additionally, the pH of the sample to which the protease composition is applied. Any desired level of buffer may be incorporated into the protease compositions so as to provide the desired pH level. In some embodiments, the protease composition has a pH of between about 4.0 and about 13.0.

In some embodiments, the buffer is selected from sodium citrate, sodium acetate, acetic acid, sodium carbonate, sodium bicarbonate, PBS, MES, Tris, Bis-Tris, ADA, aces, PIPES, MOPSO, Bis-Tris Propane, BES, MOPS, TES, HEPES, DIPSO, MOBS, TAPSO, TRIZMA, HEPPSO, POPSO, TEA, EPPS, Tricine, Gly-Gly, Bicine, HEPBS, TAPS, AMPD, TABS, AMPSO, CHES, CAPSO, AMP, CAPS, CABS, and combinations thereof.

e. Other Ingredients

In some embodiments, the protease composition further comprises one or more additional agents, such as complexing agents, chaotropic agents, reducing agents or salts. Examples of the complexing agents include, but not limited to, ethylenediamine-N,N,N',N'-tetraacetic acid (EDTA), ethylene glycol bis(2-aminoethyl ether)-N,N,N',N'-tetraacetic acid (EGTA), sodium citrate or mixtures thereof.

Examples of chaotropic agents include, without limitation, trichloroacetates, thiocyanates (including guanidinium (or "guanidine") isothiocyanate), perchlorates (such as sodium perchlorate), iodides (such as sodium iodide, potassium iodide), guanidinium hydrochloride, and urea.

Examples of reducing agents include, without limitation, dithiothreitol (DTT), dithioerythritol (DTE), dithiobutylamine (DTBA), or tris(2-carboxyethyl) phosphine (TCEP), sodium thiosulphate, β-mercaptoethanol or mixtures thereof.

Examples of salts include, without limitation, NaCl, KCl or LiCl, alkaline earth metal halides, such as, $CaCl_2$ or $MgCl_2$, ammonium salts, such as, ammonium chloride or ammonium sulfate, lithium sulfate or mixtures thereof.

In some embodiments, the additional agent comprises CTAB, EDTA, EGTA, DTT, 2-mercaptoethanol, polyethylene glycol, a coloring agent, glycerin, guanidinium chloride, guanidinium thiocyanate, urea, calcium salt, sodium salt, potassium salt, magnesium salt or a mixture thereof.

Suitable coloring agents include food, drug, and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide. Other examples of coloring agents include known azo dyes, organic or inorganic pigments, or coloring agents of natural origin.

In some embodiments, a kit comprises a ready-to-use protease composition, as described above. The kit can be used for stabilization, conservation, transportation and storage of a sample containing nucleic acids. In some embodiments, the kit comprises an instruciton material that contains instructoins for using the kit or the protease composition for stabilization, conservation, transportation and storage of a sample containing nucleic acids and/or protein proteolytic degradation.

In one embodiment, the kit includes (a) a container that contains a ready-to-use protease composition as disclosed; and optionally (b) informational or instruction material. The informational material can be descriptive, instructional, marketing or other material that relates to the methods described herein and/or the use of the disclosed protease composition, for example, on degrading a protein or stabilizing nucleic acid molecule from a sample containing a protein. In some embodiments, the kit also includes an additional agent contained in the same or different container from the protease composition. For example, the kit may include a detergent provided in a separate container or a separate compartment from the protease composition.

In some embodiments, the kit may also include an apparatus (e.g., test tube or device) for collecting a sample. The apparatus can be pre-loaded with a protease composition or can be empty, but suitable for loading.

In some embodiments, the apparatus may include two or more compartments. For example, one compartment may contain a protease composition as described, and another compartment may be used to receive a sample. In some embodiments, the two or more compartments are so arranged that the protease composition can be readily mixed/incubated with the sample within or outside the apparatus.

In addition to the protease composition, the kit can also include other agents, such as a solvent or buffer, an adjuvant, a stabilizer, or a preservative. The kit may optionally include a device suitable for collecting the sample, e.g., a tube, container or other suitable collecting device.

B. METHODS OF USE

In another aspect, this disclosure further provides a method of stabilizing nucleic acid molecules in a sample, for example, by degrading proteins (e.g., DNAse, RNAse) in the sample. In some embodiments, the method comprises contacting the sample with the kit as described above.

Once the DNase and RNase and other proteins are degraded in the samples, the nucleic acids are stable at room temperature for days, months or years. The samples can be stored and arrange for future processing or batch processing. However, the protein degrading enzymes, such as proteinase K are usually biologically unstable in the liquid form, and there is a need for improving the stability of protein degrading enzymes. Some detergent is in liquid form and easily oxidized, resulting in loss of function, and some detergents are dry powder but difficult to distribute required dose amount. Accordingly, this disclosure provides a simple and easy-to-use methodology to perform nucleic acid detection and purification.

The starting samples may be any material containing nucleic acid, including, for example, foods and allied products, clinical and environmental samples. The sample generally contains a biological sample, which may contain any viral, bacterial or cellular material, including all prokaryotic or eukaryotic cells, viruses, bacteriophages, mycoplasmas, protoplasts, and organelles. Such biological material may thus comprise all types of mammalian and non-mammalian animal cells, plant cells, algae including blue-green algae, fungi, bacteria, protozoa etc. Representative samples include whole blood and blood-derived products such as plasma, serum and buffy coat, urine, saliva, nasopharyngeal swab, oropharyngeal swab, lung lavage, feces, cerebrospinal fluid or any other bodily fluids, tissues, cell cultures, cell suspensions, etc.

In some embodiments, the sample is a biological sample comprising a nucleic acid molecule. In some embodiments, the biological sample comprises human or animal tissue, plasma, serum, blood, saliva, amniotic fluid, aqueous humor, vitreous humor, bile, breast milk, cerebrospinal fluid, cerumen, chyle, chyme, endolymph, perilymph, diarrhea, stool, female ejaculate, gastric acid, gastric juice, lymph, mucus, pericardial fluid, peritoneal fluid, pleural fluid, purulent exudate, rheum, cebum, semen, sputum, synovial fluid, lacrimal fluid, sweat, vaginal secretions, vomit, urine, cultured cell or supernatant, or plant or plant part thereof.

In some embodiments, the method comprises: (a) contacting the sample with a kit described above; and (b) incubating the mixture for a predetermined period of time, thereby stabilizing the nucleic acid for transportation or storage; and (c) optionally detecting and/or isolating the nucleic acid molecule from the sample.

The nucleic acids (e.g., DNA, RNA) in the sample treated with a protease composition as disclosed can be further purified with the aid of any suitable method, for example, by binding to a silica matrix using, for example, the QIAGEN QIAamp FFPE Kit or QIAGEN RNeasy Mini or Micro Kit.

For the purpose of the invention, the term "nucleic acids" includes all nucleic acids known to the person skilled in the art, for example, natural or synthetic nucleic acids, and also nucleic acids artificially introduced into the sample, single- and double-stranded nucleic acids, straight-chain, branched or circular nucleic acids, cDNA, RNA, in particular mRNA, siRNA, miRNA, snRNA, tRNA, hnRNA or ribozymes, DNA, in particular genomic or plastid DNA or DNA from organelles, and also nucleic acids of infectious origin.

In some embodiments, the method may further comprise a step for detecting the isolated and/or purified nucleic acids, preferably selected from the group comprising amplification techniques, in particular PCR, qPCR, RT-PCR, qRT-PCR, and amplification of the entire genomic DNA (whole genome amplification), gel electrophoresis, blotting techniques, in particular Southern blotting and Northern blotting, microarray analyses, restriction fragment length polymorphism analyses (RFLP analyses), SAGE (serial analysis of gene expression), sequencing including NextGeneration sequencing and RNA sequencing, single nucleotide polymorphism analyses (SNP analyses), mutation analyses, epigenetic analyses, in particular analyses of methylation patterns or combinations thereof.

C. ADDITIONAL FILM COMPOSITIONS

Also provided in this disclosure is the use of a polymer matrix to prepare film compositions containing one or more enzymes or reagents with or without protease. For example, enzymes or reagents can be manufactured with one or more polymers to form a water-soluble film composition, so that enzyme/polymer master mix can be conveniently shipped and stored at ambient temperature, thus eliminating the need for cold chain, cutting the carbon footprint, and significantly reducing overall cost. The enzymes or reagents may include, without limitation, primer/probe, dTTP, ligase, reverse-transcriptase, Taq polymerase, and other reagents used in the molecular biology techniques.

D. DEFINITIONS

To aid in understanding the detailed description of the compositions and methods according to the disclosure, a few express definitions are provided to facilitate an unambiguous disclosure of the various aspects of the disclosure. Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "contacting," when used in reference to any set of components, includes any process whereby the components to be contacted are mixed into the same mixture (for example, are added into the same compartment or solution), and does not necessarily require actual physical contact between the recited components. The recited components can be contacted in any order or any combination (or sub-combination) and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C.

"Sample," "test sample," and "patient sample" may be used interchangeably herein. The sample can be a sample of serum, urine plasma, amniotic fluid, cerebrospinal fluid, cells, or tissue. Such a sample can be used directly as obtained from a patient or can be pretreated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as nucleic acid. The sample may be any tissue sample from the subject. The sample may comprise protein from the subject.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise. In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

E. EXAMPLES

Proteinase K Film Formulation

Example #A1

| Ingredients | (mg) | Dry % |
| --- | --- | --- |
| Proteinase K | 4 | 67% |
| Glycerin | 0.3 | 5% |
| Yellow #6 | 0.003 | 0.05% |
| PVA4-88, USP | 0.72 | 12.00% |
| PVA18-88, USP | 0.977 | 16.28% |
| SUM | 6.00 | 100% |

Example #A2

| Ingredients | (mg) |
| --- | --- |
| Proteinase K | 4 |
| Glycerin | 0.6 |
| Water | 0 |
| FD& C Green #3 | 0.003 |
| Pullulan | 1.397 |
| SUM | 6.00 |

Proteinase K Film Preparation Methods

1. Prepare polymer (PVA & Pullulan) stock solutions 10%-50% with 1% $CaCl_2$.
2. Add other ingredients into the solution;
3. Mix all ingredients at 300 rpm for 30 minutes and de-air the mixture;
4. Coat the mixture on a release liner at a thickness of 300 μm-500 μm and air-dry in a hood for 3 hours;
5. Die-cut the dry product into small films of approximately 6 mg each.

Example #A3

| Ingredients | (mg) |
| --- | --- |
| Proteinase K | 4 |
| Glycerin | 0.6 |
| EDTA | 0.1 |
| CTAB | 1 |
| Water | 0 |
| FD&C Green#3 | 0.003 |
| PVA | 1.397 |
| SUM | 7.1 |

SDS Formulation

Example #S1

| Ingredients | (mg) |
| --- | --- |
| SDS | 40 |
| Glycerin | 6.6 |
| PVA4-88, USP | 4.4 |
| PVA18-88, USP | 4 |
| SUM | 55.0 |

Example #S2

| Ingredients | (mg) |
| --- | --- |
| SDS | 40 |
| CTAB | 10 |
| CaCl | 1 |
| EDTA | 10 |
| Glycerin | 6.6 |
| PVA4-88, USP | 4.4 |
| PVA18-88, USP | 4 |
| SUM | 76.00 |

Solid SDS Preparation Methods

1. Prepare polymer (PVA4-88 & PVA18-88) stock solutions 10%-50%;
2. Add other ingredients into the solution;

3. Mix all ingredients at 300 rpm for 30 minutes;
4A. Coat the mixture on a release liner at a thickness of 900 µm-2 mm and dry at 80 C for 30 min to 1 hour;
5. Die-cut the dry product into small pellets of approximately 55 mg each.
5B. Individual pellets can be harvested after drying.
4B, alternatively for steps 4&5, use a syringe to push droplets (0.12 g-0.2 g) on silicon-coated myla or silicon coated paper, dry at 80 C for 30 min-1 hour Example #4

Proteinase K and SDS Can be Prepared in a Single Solid Form with the Formulation Below

| Ingredients | (mg) | % |
|---|---|---|
| Proteinase K | 4 | 7% |
| SDS | 40 | 68% |
| Glycerin | 6.6 | 11% |
| FD&C Green#3 | 0.01 | 0% |
| PVA4-88, USP | 4.4 | 7% |
| PVA18-88, USP | 4 | 7% |
| | 59.01 | 100% |

Single Solid Form of Proteinase K and SDS in Example #4
Preparation Methods
1. Prepare polymer (PVA4-88 & PVA18-88) stock solutions 10%-50%.
2. Add other ingredients to the solution.
3. Mix all ingredients at 300 rpm for 30 minutes.
4A. Coat the mixture on a release liner at a thickness of 900 µm-2 mm and dry at 60-80 C for approximately 30 min-2 hour.
5. Die-cut the dry product into small pellets of approximately 59 mg each.

As described herein, the protease composition as a film formulation with or without detergent was prepared. In one example, the detergent SDS was provided separately from the protease composition. The single FIGURE shows the activity of proteinase K as provided in the disclosed film composition on human plasma. Proteinase K in different amounts (0.2 mg, 0.3 mg, 0.5 mg, 0.6 mg, 1 mg, and 1.2 mg) was mixed with the plasma sample and incubated at 55° C. for 30 minutes.

Example #5

Proteinase K and SDS Can be Prepared in a Single Pouch with the Formulation Below

| Ingredients | (mg) | % |
|---|---|---|
| Proteinase K | 4 | 7% |
| SDS | 40 | 68% |
| FD&C Green#3 | 0.01 | 0% |
| PVA Polymer membrane | 15.4 | 25% |

Single Solid Pouch of Proteinase K and SDS in Example #5
Preparation Methods
1. Weigh proteinase K and SDS according to the above table.
2. Mix well.
3. Cut and weigh PVA membrane according to the above table.
4. Create a bag by sealing three sides of the bag.
5. Add the proteinase K and SDS mixture.
6. Seal the bag with the proteinase K and SDS mixture inside the bag.

As described herein, the protease composition as a pouch formulation was prepared, where the protease (with or without detergent) is encapsulated in a liquid soluble PVA membrane.

What is claimed is:

1. A kit consisting essentially of a protease composition comprising a protease, and a polymer matrix formed of a polymer, wherein the polymer matrix is in the form of
a film where the protease is distributed therewithin,
wherein the polymer matrix is dissolvable in an aqueous phase and capable of releasing the protease from the kit upon contacting the aqueous phase, wherein the polymer matrix is in an amount of between about 10 wt % and about 34 wt %, wherein the protease is in an amount of between about 0.5 wt % and about 85 wt %, and wherein the film has a thickness of between about 10 µm and about 500 mm.

2. The kit of claim 1, wherein the protease is a serine protease.

3. The kit of claim 1, wherein the protease is selected from proteinase K, trypsin, chymotrypsin, papain, pepsin, pronase, endoproteinase Lys-C and cyanogen bromide, neutral, is heat-sensitive serine protease (NHSSP), and mixtures thereof.

4. The kit of claim 1, wherein the protease is proteinase K.

5. The kit of claim 1, wherein the polymer is selected from poly(vinyl) alcohol (PVOH), sodium carboxymethyl cellulose (NaCMC), hydroxyethyl cellulose (HEC), hydroxypropyl cellulose (HPC), hydroxypropylmethylcellulose (HPMC), polyvinylpyrrolidone (PVP), hydroethylmethyl cellulose (HEMP), pullulan, gelatin, modified starch, polyethylene oxide, polyacrylate, and combinations thereof.

6. The kit of claim 1, wherein the protease composition further comprises a detergent.

7. The kit of claim 6, wherein the detergent is selected from deoxycholate, sodium dodecyl sulfate (SDS), Lithium dodecyl sulfate (LDS), N-lauroyl sarcosine, Sarkosyl, cetyltrimethylammoniumbromide (CTAB), Triton X-100, octyl glucoside, polyoxyethylene(9)dodecyl ether, digitonin, octylphenyl polyethylene glycol, n-octyl-beta-D-glucopyranoside (betaOG), n-dodecyl-beta, Polysorbate 20, polyethylene glycol sorbitan monolaurate, Polysorbate 80, polyethylene glycol sorbitan monooleate, polidocanol, n-dodecyl beta-D-maltoside (DDM), NP-40, nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside), polyethylene glycol monoalkyl ether, polyoxyethylene distyrenated phenyl ether, polyoxyethylene 10 lauryl ether (C12E10), Chaps, zwitterion 3-14, 3-[(3-cholamidopropyl)dimethylarnmonio]-1-propancsulfonate, and combinations thereof.

8. The kit of claim 1, wherein the protease composition further comprises a buffer selected from sodium citrate, sodium acetate, acetic acid, sodium carbonate, sodium bicarbonate, MES, Tris, Bis-Tris, ADA, aces, PIPES, MOPSO, Bis-Tris Propane, BES, MOPS, TES, HEPES, DIPSO, MOBS, TAPSO, HEPPSO, POPSO, TEA, EPPS, Tricine, Gly-Gly, Bicine, HEPBS, TAPS, AMPD, TABS, AMPSO, CHES, CAPSO, AMP, CAPS, CABS, and combinations thereof.

9. The kit of claim 1, wherein the protease composition has a pH of between about 4.0 and about 13.0.

10. The kit of claim 1, wherein the protease composition further comprises an additional agent comprising cetyltrimethylammonium bromide (CTAB), EDTA, EGTA, DTT, 2-mercaptoethanol, polyethylene glycol, a coloring agent, glycerin, guanidinium chloride, guanidinium thiocyanate, urea, calcium salt, sodium salt, potassium salt, magnesium salt or a mixture thereof.

11. The kit of claim 1, wherein the polymer matrix is in an amount of between about 15 wt % and about 30 wt %.

12. The kit of claim 1, comprising:
   (i) between about 1 wt % and about 80 wt % of proteinase K;
   (ii) between about 5 wt % and about 34 wt % of PVOH;
   (iii) between about 0.2 wt % and about 80 wt % of SDS; and
   (iv) between about 0 wt % and about 10 wt % of glycerin.

13. The kit of claim 1, wherein the protease composition further comprises a detergent provided in a separate container or a separate compartment from the protease.

14. A method of degrading a protein in a sample, comprising contacting the sample with the kit of claim 1.

15. The method of claim 14, wherein the sample is a biological sample comprising a nucleic acid molecule.

16. The method of claim 15, wherein the biological sample comprises human or animal tissue, plasma, serum, blood, saliva, amniotic fluid, aqueous humor, vitreous humor, bile, breast milk, cerebrospinal fluid, cerumen, chyle, chyme, endolymph, perilymph, diarrhea, stool, female ejaculate, gastric acid, gastric juice, lymph, mucus, pericardial fluid, peritoneal fluid, pleural fluid, purulent exudate, rheum, cebum, semen, sputum, synovial fluid, lacrimal fluid, sweat, vaginal secretions, vomit, urine, cultured cell or supernatant, or plant or plant part thereof.

17. A method of stabilizing nucleic acid molecule from a sample containing a protein, comprising:
   (a) contacting the sample with the kit of claim 1;
   (b) incubating the mixture for a predetermined period of time, thereby allowing the protein in the sample to be degraded through proteolysis by the protease, thereby stabilizing the nucleic acid for transportation or storage; and
   (c) optionally isolating the nucleic acid molecule from the sample.

18. A kit, comprising: a protease composition comprising a protease, a polymer matrix formed of a polymer, and optionally an instruction material, wherein the polymer matrix is in the form of:
   (a) a film where the protease is distributed therewithin; or
   (b) a pouch where the protease is encapsulated therein,
   wherein the polymer matrix is dissolvable in an aqueous phase and capable of releasing the protease from the kit upon contacting the aqueous phase, and wherein the composition comprises:
   (i) between about 1 wt % and about 80 wt % of proteinase K;
   (ii) between about 5 wt % and about 34 wt % of PVOH;
   (iii) between about 0.2 wt % and about 80 wt % of SDS; and
   (iv) between about 0 wt % and about 10 wt % of glycerin.

19. A protease composition comprising a protease and a polymer matrix formed of a polymer, wherein the polymer matrix is in the form of:
   (a) a film where the protease is distributed therewithin; or
   (b) a pouch where the protease is encapsulated therein,
   wherein the polymer matrix is dissolvable in an aqueous phase and capable of releasing the protease from the composition upon contacting the aqueous phase, and wherein the composition comprises:
   (i) between about 1 wt % and about 80 wt % of proteinase K;
   (ii) between about 5 wt % and about 34 wt % of PVOH;
   (iii) between about 0.2 wt % and about 80 wt % of SDS; and
   (iv) between about 0 wt % and about 10 wt % of glycerin.

* * * * *